(12) United States Patent
Taylor et al.

(10) Patent No.: US 8,247,454 B2
(45) Date of Patent: Aug. 21, 2012

(54) LIQUID ANTIBACTERIAL COMPOSITIONS INCORPORATING TRICHLOROCARBANILIDE WITH REDUCED WATER ACTIVITY

(75) Inventors: Timothy J. Taylor, Phoenix, AZ (US); Priscilla S. Fox, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 890 days.

(21) Appl. No.: 12/096,896

(22) PCT Filed: Dec. 20, 2006

(86) PCT No.: PCT/US2006/049184
§ 371 (c)(1),
(2), (4) Date: Oct. 13, 2008

(87) PCT Pub. No.: WO2007/092090
PCT Pub. Date: Aug. 16, 2007

(65) Prior Publication Data
US 2009/0156684 A1    Jun. 18, 2009

Related U.S. Application Data

(60) Provisional application No. 60/755,463, filed on Dec. 30, 2005.

(51) Int. Cl.
*A61K 31/17* (2006.01)
(52) U.S. Cl. .......................... 514/588; 514/595; 514/596
(58) Field of Classification Search ................. 514/588, 514/595, 596
See application file for complete search history.

(56) References Cited

FOREIGN PATENT DOCUMENTS

| DE | 190379 A1 | 7/1970 |
|---|---|---|
| WO | WO 96/21426 | 7/1996 |
| WO | WO 98/42820 | 10/1998 |
| WO | WO 99/57238 | 11/1999 |
| WO | WO 01/13868 | 3/2001 |
| WO | WO 02/13776 | 2/2002 |

OTHER PUBLICATIONS

PCT Notification of the Transmittal of the International Search Report and The Written Opinion of the International Searching Authority, or the Declaration for PCT/US2006/049184, dated Sep. 24, 2007.

*Primary Examiner* — Renee Claytor
(74) *Attorney, Agent, or Firm* — David K. Benson

(57) ABSTRACT

A liquid antibacterial soap comprising trichlorocarbanilide, wherein the composition includes, 0.1-5 wt. % trichlorocarbanilide, 0-40 wt. % water, 0.1-40 wt. % of a surfactant or mixture of surfactants, 10-60 wt. % of lower glycols to render the composition visually clear and stable, and 0.1-10 wt. % of a mixture of additional adjuvant ingredients.

17 Claims, No Drawings

LIQUID ANTIBACTERIAL COMPOSITIONS INCORPORATING TRICHLOROCARBANILIDE WITH REDUCED WATER ACTIVITY

CROSS-REFERENCE TO RELATED APPLICATIONS

This application is a U.S. National Phase filing under 35 U.S.C. 371 and claims priority to PCT Application No. PCT/US2006/049184, entitled "LIQUID ANTIBACTERIAL COMPOSITIONS INCORPORATING TRICHLOROCARBANILIDE WITH REDUCED WATER ACTIVITY," which was filed on Dec. 20, 2006, which application claims priority to U.S. Provisional Patent Application Ser. No. 60/755,463, entitled "LIQUID ANTIBACTERIAL COMPOSITIONS INCORPORATING TRICHLOROCARBANILIDE WITH REDUCED WATER ACTIVITY," which was filed Dec. 30, 2005, both of which are incorporated herein by reference.

FIELD OF INVENTION

The present invention relates generally to a liquid antibacterial composition and more particularly, to a liquid antibacterial composition incorporating trichlorocarbanilide.

BACKGROUND OF THE INVENTION

In general, trichlorcarbanilide, or triclocarban (TCC, chemically known as 3,4,4'- trichlorocarbanilide) is a widely used antibacterial compound in the art of personal cleansing compositions, and primarily used in solid bar soap compositions. TCC exhibits extremely low water solubility and is therefore not considered conducive for a liquid compositional based product. As TCC is used in the solid bar composition form, TCC is generally considered to be effective against Gram-positive bacteria, yet not as effective against Gram-negative bacteria; i.e., TCC is not considered to be a broad-spectrum biocide.

Currently, a large percentage of the consuming public has shown an attraction to liquid body cleansing products, as evidenced by the broad acceptance and popularity of liquid body wash products and liquid hand soaps in the marketplace. These liquid compositions are traditionally aqueous in character. But due to its virtual insolubility in water, TCC has not been used in aqueous cleansing compositions and thus, formulators have been forced to rely on other antibacterial agents to provide antibacterial benefits to consumers.

Therefore, there exists a need to provide a stable, aqueous-based, liquid cleansing composition, incorporating TCC as the antibacterial agent so a user may enjoy the benefits of using a liquid soap in conjunction with the effective antibacterial agent, TCC.

SUMMARY OF THE INVENTION

While the way in which the present invention addresses the disadvantages of the prior art will be discussed in greater detail below, in general, the present invention provides for a liquid antibacterial composition incorporating trichlorocarbanilide, which offers significant advantages to the user of the composition which the prior art does not address.

For example, in accordance with various embodiments of the present invention, a liquid antibacterial composition incorporating trichlorocarbanilide is described which provides a user with the benefit of a trichlorocarbanilide based soap product in a liquid form. To accomplish such, it has been found that liquid compositions can be effectively formulated using TCC if the water content of the formulation is kept at or below a predetermined amount. As an added benefit, unlike the TCC based solid bar compositions, it has been found that the TCC based liquid composition is effective against Gram-negative bacteria in addition to Gram-positive bacteria.

DETAILED DESCRIPTION

The following descriptions are of exemplary embodiments of the invention only, and are not intended to limit the scope, applicability or configuration of the invention in any way. Rather, the following description is intended to provide a convenient illustration for implementing various embodiments of the invention. As will become apparent, various changes may be made in the composition, function and arrangement of the elements described herein without departing from the spirit and scope of the invention. For example, though not specifically described; various configurations of liquid antibacterial compositions incorporating trichlorocarbanilide with reduced water activity, and various types of additives and other examples now known or as yet unknown in the art, may be understood to fall within the scope of the present invention.

That said, in general, and in accordance with various embodiments of the present invention, a liquid antibacterial composition in accordance with various examples of the present invention comprises 3,4,4'-trichlorocarbanilide, water, surfactant, and a co-solvent such as, for example, a lower glycol, the composition exhibiting increased anti-bacterial efficacy.

In accordance with an exemplary embodiment of the present invention, a liquid antibacterial composition comprises TCC, for example, present from about 0.01 to about 10 weight percent of the liquid antibacterial composition. In yet another example of the invention, the TCC is preferably present in the amount from about 0.05 to about 7.5 weight percent of the liquid antibacterial composition. In still another example of the invention, the TCC is most preferably present in the amount from about 0.1 to about 5 weight percent of the liquid antibacterial composition.

In accordance with an exemplary embodiment of the present invention, the liquid antibacterial composition also comprises a liquid carrier. In one example, the liquid carrier is water, wherein the water is comprised of distilled, deionized, or unrefined tap. Preferably, the liquid carrier comprises an amount that is at or below a predetermined point, such as saturation or the minimum water activity that causes precipitation of the TCC, wherein such point has been determined to maintain the antibacterial effectiveness of the TCC. In one example, the liquid carrier is present in an amount from about 0 to about 60 weight percent of the liquid antibacterial composition. More preferably the liquid carrier is present in an amount from about 2 to about 40 weight percent, and most preferably, present in an amount from about 3 to about 20 weight percent of the liquid antibacterial composition.

As noted above, in accordance with an exemplary embodiment of the present invention, the liquid antibacterial composition further comprises a surfactant component. In accordance with an exemplary embodiment of the present invention, the liquid antibacterial composition comprises a surfactant component in an amount from about 0.1 to about 40 weight percent of the liquid antibacterial composition. In accordance with various exemplary embodiments of the present invention, the surfactants may be chosen from the group of ammonium lauryl sulfate, sodium lauryl ether sulfate, sodium lauryl sulfosuccinate, betaines, amine oxides and the like.

In accordance with an exemplary embodiment of the present invention and as noted above, the liquid antibacterial composition comprises a co-solvent to render the liquid antibacterial composition visually clear and stable, such as, for example lower glycols. It will be appreciated by those skilled in the art that while the lower glycols may be present in an amount to render the composition visually clear and stable, this is done primarily for aesthetic purposes and the composition may comprise other glycols or elements that provide for an opaque or semi-translucent composition without detracting from the effectiveness of the liquid antibacterial soap. In accordance with an exemplary embodiment of the present invention, the lower glycols are present in an amount from about 10 to about 60 weight percent of the liquid antibacterial composition. In accordance with various exemplary embodiments of the present invention, the lower glycols may be chosen from the group of dipropylene glycol, ethoxydiglycol, PEG-8, propylene glycol and the like.

The present inventors have found that liquid antibacterial compositions in accordance with the present invention have increased efficacy as illustrated by various kill tests.

For example, compositions show a log reduction against Gram-positive bacteria of at least 3 after 30 seconds of contact at 40° C. as measured against S. aureus as measured in a time kill test. The time kill test is used as an empirical method to quantify the antibacterial effectiveness of a soap formulation and the test is discussed in greater detail below. In yet another example of the invention, the composition comprises a log reduction against Gram-negative bacteria of a least 1 after 30 seconds of contact at 40° C. as measured against E. coli as measured in a time kill test. In still another example of the invention, the liquid antibacterial composition comprises a log reduction against Gram-positive bacteria of a least 2 after 30 seconds of contact at 40° C. as measured against S. epidermidis as measured in a time kill test. In still another example, the liquid antibacterial composition comprises a log reduction against Gram-positive bacteria of a least 2 after 30 seconds of contact at 40° C. as measured against MRSA as measured in a time kill test.

As briefly mentioned above, to evidence the antibacterial effectiveness of various formulations of the liquid soap in accordance with the present invention, time kill suspension tests were conducted, whereby the survival of challenged organisms exposed to an antibacterial test formulation is determined as a function of time. In general, the time kill method is well known in the antibacterial products industry. In this test method, a diluted aliquot of the formulation is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated. All testing is generally performed in triplicate, the results are combined, and the average log reduction is reported. The choice of the contact time period is at the discretion of the investigator. Any contact time period can be chosen. Typical contact times range from 15 seconds to 5 minutes, with 30 seconds and 1 minute being typical contact times.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about $10^8$ colony-forming units per ml (cfu/ml). The table below lists the test bacterial cultures used in the following tests and include the name of the bacteria, the ATCC (American Type Culture Collection) identification number, and the abbreviation for the name of the organism used hereafter.

| Organism Name | ATCC # | Abbreviation |
|---|---|---|
| Staphylococcus aureus | 6538 | S. aureus |
| Escherichia coli | 11229 | E. coli |
| Staphylococcus epidermidis | 155 | S. epidermidis |
| Methicillin-resistant Staphylococcus aureus | 700698 | MRSA |

S. aureus is a Gram positive bacteria, as are S. epidermidis and MRSA, whereas E. coli is a Gram negative bacteria.

EXAMPLE 1

In this example, three different formulations of liquid soaps were tested using the time kill suspension test method. Table 1 summarizes the compositions of the three formulations, Formulations A, B, and a Placebo. Two formulations (Formulations A and B) were formed in accordance with various examples of the present invention. The third Placebo formulation was formed without the Ethoxydiglycol/TCC premix, not in accordance with various examples of the present invention. These three formulations, with each of the components set forth in weight percent, are as follows:

TABLE 1

| Ingredient | Formulation A (wt. %) | Formulation B (wt. %) | Placebo (wt. %) |
|---|---|---|---|
| DI Water | 35.78 | 19.97 | 42.78 |
| Polyquaternium 10 | 0.50 | 0.30 | 0.50 |
| Glycerin | 9.90 | 10.10 | 10.0 |
| Sodium laureth sulfate | 4.46 | 4.46 | 4.46 |
| Cocamidopropyl betaine | 3.06 | 3.06 | 3.06 |
| Disodium lauryl sulfosuccinate | 1.96 | 1.96 | 1.96 |
| Preservative (DMDM Hydantoin/IPBC) | 0.10 | 0.10 | 0.10 |
| Tetrasodium EDTA | 0.02 | 0.02 | 0.05 |
| Fragrance oil | 0.20 | 0.20 | 0.20 |
| Sodium chloride | 0.35 | 0.35 | 0.35 |
| PEG-8 | 5.00 | 5.00 | 5.0 |
| Ethoxydiglycol | 3.70 | 19.70 | — |
| Trichlorocarbanilide | 0.70 | 0.70 | — |
| Dipropylene glycol Total | 34.26 | 34.26 | 34.6 |

The three different formulations were tested using 75% aqueous solutions of the formulations. Each solution was added to a beaker in a water bath, stirred, and heated to approximately 40° C., which is typically the temperature at which consumers use antibacterial liquid soap for body cleansing. The solution then was inoculated with 1.0 ml of the test bacteria suspensions. The inoculum was stirred with the solution for a contact time of 30 seconds. When the contact time expired, 1.0 ml of the solution/bacteria mixture was transferred into 9.0 ml of Tryptone-Histidine-Tween Neutralizer Solution (THT). Decimal dilutions to a countable range then were made. Plate selected dilutions were produced in triplicate on TSA+plates (TSA+is Trypticase Soy Agar with Lecithin and Polysorbate 80). The plates then were incubated for 25±2 hours, and the colonies were counted for the number of survivors. The control count (numbers control) was determined by conducting the procedure as described above with the exception that THT was used in place of the test composition. The plate counts were converted to cfu/ml for the numbers control and samples, respectively, by standard microbiological methods.

The log reduction was calculated using the formula:

Log reduction=log 10 (numbers control)−log 10 (test sample survivors).

The following Table 2 correlates percent reduction in bacteria population to log reduction:

TABLE 2

| % Reduction | Log Reduction |
|---|---|
| 90 | 1 |
| 99 | 2 |
| 99.9 | 3 |
| 99.99 | 4 |
| 99.999 | 5 |

The log reduction, or alternatively the percent reduction, in bacterial populations provided by the antibacterial composition correlates to antibacterial activity. As can be seen by Table 2, a log reduction of 3-5 provides a greater percent reduction in bacteria population than a 1-3 reduction, whereas a log reduction of less than 1 provides the least percent reduction in bacteria population, for the particular contact time. Thus, a most favored antibacterial composition exhibits a 3-5 log reduction against a broad spectrum of microorganisms in a short contact time.

Table 3 summarizes the results of time kill tests performed on the solutions of the three formulations at 30 second contact time:

TABLE 3

| Formulation | S. aureus | E. coli | S. epidermidis | MRSA |
|---|---|---|---|---|
| A | 3.22 | 1.76 | 2.10 | 2.40 |
| B | >4.98 | 5.01 | >4.84 | >4.71 |
| Placebo | 2.03 | 1.82 | 1.04 | 1.06 |

In sum, and with reference to Table 3, it is clear that among the examples, formulation B provides the greatest percent reduction in bacteria population, wherein the liquid antibacterial composition comprises a log reduction against Gram-negative bacteria of almost 5 after 30 seconds of contact at 40° C. as measured against all bacterium listed, as measured in a time kill test. However, one skilled in the art will appreciate that such results are exemplary results from an exemplary formulation and other formulations may be prepared that provide substantially similar results.

Returning to an exemplary embodiment of the present invention, the liquid antibacterial composition, in accordance with the present invention may also contain other optional adjuvant ingredients that are present in sufficient amount to perform their intended function and that do not adversely affect the antibacterial efficacy of the liquid soap composition. Such optional ingredients typically are present from about 0.1 to about 10 weight percent of the composition. For example, the liquid antibacterial composition may include one or more of the following conventional additives, such as, for example, fragrances, polymers, preservatives, skin care aids, dyes, pH adjusters, chelating agents, stabilizers and combinations thereof.

The preferred processing of the formulation includes a premix to disburse the TCC. The TCC can be utilized from 0.1 to 16 percent in Ethoxydiglycol and the like. The TCC is added to mixing glycol and the premix can be heated depending on the formulation but is not required. The premix is added to the main batch near the end of the processing or can be stored for later usage.

Lastly, it should be appreciated that the present invention has been described above with reference to various exemplary embodiments. Those skilled in the art will recognize that changes and modifications may be made to these embodiments without departing from the scope of the present invention. Such changes or modifications are intended to be included within the scope of the present invention as set forth herein.

What is claimed is:

1. A liquid antibacterial composition comprising:
   3,4,4'- trichlorocarbanilide present in an amount from about 0.01 to about 10 weight percent of said liquid antibacterial composition;
   water present in an amount from about 3 to about 20 weight percent of said liquid antibacterial composition;
   one or more surfactants present in an amount from about 0.1 to about 40 weight percent of said liquid antibacterial composition;
   one or more co-solvents present in an amount from about 10 to about 60 weight percent of said liquid antibacterial composition; and
   optionally one or more ingredients selected from a group comprising: fragrances, polymers, preservatives, skin care aids, dyes, pH adjusters, chelating agents, stabilizers and combinations thereof, present in an amount from about 0.1 to about 10 weight percent of said liquid antibacterial composition.

2. The liquid antibacterial composition of claim 1, wherein said trichlorcarbanilide is present in an amount from about 0.05 to about 7.5 weight percent of said liquid antibacterial composition.

3. The liquid antibacterial composition of claim 2, wherein said trichlorcarbanilide is present in an amount from about 0.1 to about 5 weight percent of said liquid antibacterial composition.

4. The liquid antibacterial composition of claim 1, wherein said surfactant is selected from a group comprising: ammonium lauryl sulfate, sodium lauryl ether sulfate, sodium lauryl sulfosuccinate, betaines, amino oxides and combinations thereof.

5. The liquid antibacterial composition of claim 1, wherein said co-solvent is a lower glycol.

6. The liquid antibacterial composition of claim 5, wherein said lower glycol is selected from a group comprising: dipropylene glycol, ethoxydiglycol, PEG-8, propylene glycol and combinations thereof.

7. The liquid antibacterial composition of claim 1 comprising a pH from about 4 to about 9.

8. The liquid antibacterial composition of claim 7 comprising a pH from about 5 to about 8.

9. The liquid antibacterial composition of claim 8 comprising a pH from about 5.5 to about 7.5.

10. The liquid antibacterial composition of claim 1, wherein the composition exhibits a log reduction against Gram-positive bacteria of a least 2.

11. The liquid antibacterial composition of claim 10, wherein the composition exhibits a log reduction against Gram-positive bacteria of a least 3.

12. The liquid antibacterial composition of claim 1, wherein the composition exhibits a log reduction against Gram-negative bacteria of a least 2.

13. The liquid antibacterial composition of claim 12, wherein the composition exhibits a log reduction against Gram-negative bacteria of a least 3.

14. The liquid antibacterial composition of claim 1, wherein the composition exhibits a log reduction against Gram-positive bacteria of a least 3 after 30 seconds of contact at 40° C. as measured against *Staph aureus* as measured in a time kill test.

15. The liquid antibacterial composition of claim 1, wherein the composition exhibits a log reduction against Gram-negative bacteria of a least 1 after 30 seconds of contact at 40° C. as measured against *E coli* as measured in a time kill test.

16. The liquid antibacterial composition of claim 1, wherein the composition exhibits a log reduction against Gram-positive bacteria of a least 2 after 30 seconds of contact at 40° C. as measured against *S. epidermidis* as measured in a time kill test.

17. The liquid antibacterial composition of claim 1, wherein the composition exhibits a log reduction against Gram-positive bacteria of a least 2 after 30 seconds of contact at 40° C. as measured against MRSA as measured in a time kill test.

* * * * *